US009872634B2

(12) United States Patent
Chan et al.

(10) Patent No.: US 9,872,634 B2
(45) Date of Patent: Jan. 23, 2018

(54) RESPIRATORY RATE MEASUREMENT USING A COMBINATION OF RESPIRATION SIGNALS

(71) Applicant: Vital Connect, Inc., Campbell, CA (US)

(72) Inventors: Alexander Chan, Campbell, CA (US); Ravi Narasimhan, Sunnyvale, CA (US)

(73) Assignee: Vital Connect, Inc., San Jose, CA (US)

( * ) Notice: Subject to any disclaimer, the term of this patent is extended or adjusted under 35 U.S.C. 154(b) by 418 days.

(21) Appl. No.: 13/763,391

(22) Filed: Feb. 8, 2013

(65) Prior Publication Data

US 2014/0228692 A1 Aug. 14, 2014

(51) Int. Cl.
*A61B 5/08* (2006.01)
*A61B 5/0472* (2006.01)
(Continued)

(52) U.S. Cl.
CPC .............. *A61B 5/08* (2013.01); *A61B 5/002* (2013.01); *A61B 5/02405* (2013.01);
(Continued)

(58) Field of Classification Search
CPC ....... A61B 5/0205; A61B 5/08; A61B 5/0803; A61B 5/0816; A61B 5/0809; A61B 5/113; A61B 5/1135
See application file for complete search history.

(56) References Cited

U.S. PATENT DOCUMENTS 8,185,191 B1 * 5/2012 Shapiro .............. A61B 5/0006
600/500
2007/0135726 A1 6/2007 Ye et al.
(Continued)

FOREIGN PATENT DOCUMENTS

JP 2005253610 A 9/2005
WO 2011032132 A2 3/2011
(Continued)

OTHER PUBLICATIONS

Chiarugi et al. "Measurement of Heart Rate and Respiratory Rate Using a Textile-Based Wearable Device in Heart Failure Patients," Computers in Cardiology, 2008, v. 35, p. 901-904.*
(Continued)

*Primary Examiner* — Charles A Marmor, II
*Assistant Examiner* — Thaddeus Cox
(74) *Attorney, Agent, or Firm* — Brundidge & Stanger, P.C.

(57) ABSTRACT

A method and system for measuring respiratory rate are disclosed. In a first aspect, the method comprises measuring at least one respiration signal and filtering the respiration signal using a lowpass filter. The method includes peak-picking the respiration signal to determine the respiratory rate and determining a quality metric of the respiratory rate. In a second aspect, the system comprises a wireless sensor device coupled to a user via at least one electrode, wherein the wireless sensor device includes a processor and a memory device coupled to the processor, wherein the memory device stores an application which, when executed by the processor, causes the processor to carry out the steps of the method.

7 Claims, 8 Drawing Sheets

(51) Int. Cl.
*A61B 5/00* (2006.01)
*A61B 5/024* (2006.01)
*A61B 5/113* (2006.01)
*A61B 5/087* (2006.01)

(52) U.S. Cl.
CPC .......... *A61B 5/0472* (2013.01); *A61B 5/0816* (2013.01); *A61B 5/4818* (2013.01); *A61B 5/7221* (2013.01); *A61B 5/082* (2013.01); *A61B 5/087* (2013.01); *A61B 5/0809* (2013.01); *A61B 5/113* (2013.01); *A61B 5/1135* (2013.01); *A61B 5/6801* (2013.01)

(56) References Cited

U.S. PATENT DOCUMENTS

| | | | |
|---|---|---|---|
| 2008/0082003 A1* | 4/2008 | Deng et al. | 600/484 |
| 2010/0004552 A1* | 1/2010 | Zhang et al. | 600/529 |
| 2010/0152600 A1* | 6/2010 | Droitcour et al. | 600/534 |
| 2010/0331715 A1 | 12/2010 | Addison et al. | |
| 2011/0071406 A1 | 3/2011 | Addison et al. | |
| 2011/0172504 A1* | 7/2011 | Wegerich | 600/301 |
| 2011/0173149 A1* | 7/2011 | Schon | 706/48 |
| 2011/0257554 A1 | 10/2011 | Banet et al. | |
| 2011/0270058 A1 | 11/2011 | Price et al. | |
| 2011/0306858 A1 | 12/2011 | Watson et al. | |
| 2012/0227043 A1* | 9/2012 | Johansson et al. | 718/100 |
| 2014/0101192 A1* | 4/2014 | Sabah et al. | 707/769 |
| 2014/0180044 A1* | 6/2014 | Addison | A61B 5/14551 600/324 |

FOREIGN PATENT DOCUMENTS

| | | |
|---|---|---|
| WO | 2011098944 A1 | 8/2011 |
| WO | 2013179018 A1 | 12/2013 |

OTHER PUBLICATIONS

Scholkmann et al., "An Efficient Algorithm for Automatic Peak Detection in Noisy Periodic and Quasi-Periodic Signals," Algorithms, Nov. 21, 2012, v. 5, p. 588-603.*
http://www.mathcentre.ac.uk/resources/uploaded/mc-bus-expconstant-2009-1.pdf, retrieved on Apr. 3, 2015.*
Mason, L. Signal Processing Methods for Non-Invasive Respiration Monitoring. Dissertation, Department of Engineering Science, University of Oxford. 2002.
Chiarugi, F et al. Adaptive Threshold QRS Detector With Best Channel Selection Based on a Noise Rating System. Computer in Cardiology. 2007; vol. 34, pp. 157-160.
Nemati, S et al. Data Fusion for Improved Respiration Rate Estimation. EURASIP Journal on Advances in Signal Processing. 2010.
Extended European Search Report (EESR) dated Aug. 19, 2016.
Japanese Office Action (Notice of Reasons for Rejection) dated Aug. 16, 2016.

* cited by examiner

US 9,872,634 B2

RESPIRATORY RATE MEASUREMENT USING A COMBINATION OF RESPIRATION SIGNALS

FIELD OF THE INVENTION

The present invention relates to sensors, and more particularly, to a sensor device utilized to measure respiratory rate using a combination of respiration signals.

BACKGROUND

Respiratory rate (RR) is an important vital sign that is useful for examining periods of distress. High and low respiratory rates are often symptoms of serious diseases including heart failure (Cheyne-Stokes breathing), obstructive sleep apnea (cessation of breathing), and metabolic acidosis (hyperventilation). The accurate measurement of respiratory rates using non-intrusive sensors enables the continuous monitoring of a person's respiratory rate.

Conventional methods of measuring a person's respiratory rate include measuring each breath when the person is at rest over a predetermined time period by counting how many times the person's chest rises. Devices such as stethoscopes are often utilized by doctors to assist as well. However, these conventional methods are inefficient, intrusive, and require time consuming analysis to measure the respiratory rate. Therefore, there is a strong need for a cost-effective solution that overcomes the above issue by utilizing a combination of sensors and signals to measure RR thereby providing increased accuracy over the measurement of RR using any single sensor/signal. The present invention addresses such a need.

SUMMARY OF THE INVENTION

A method and system for measuring respiratory rate are disclosed. In a first aspect, the method comprises measuring at least one respiration signal and filtering the respiration signal using a lowpass filter. The method includes peak-picking the respiration signal to determine the respiratory rate and determining a quality metric of the respiratory rate.

In a second aspect, the system comprises a wireless sensor device coupled to a user via at least one electrode, wherein the wireless sensor device includes a processor and a memory device coupled to the processor, wherein the memory device stores an application which, when executed by the processor, causes the processor to measure at least one respiration signal and filter the respiration signal using a lowpass filter. The system further causes the processor to peak-pick the respiration signal to determine the respiratory rate and to determine a quality metric of the respiratory rate.

BRIEF DESCRIPTION OF THE DRAWINGS

The accompanying figures illustrate several embodiments of the invention and, together with the description, serve to explain the principles of the invention. One of ordinary skill in the art will recognize that the embodiments illustrated in the figures are merely exemplary, and are not intended to limit the scope of the present invention.

DETAILED DESCRIPTION

Figure 1:
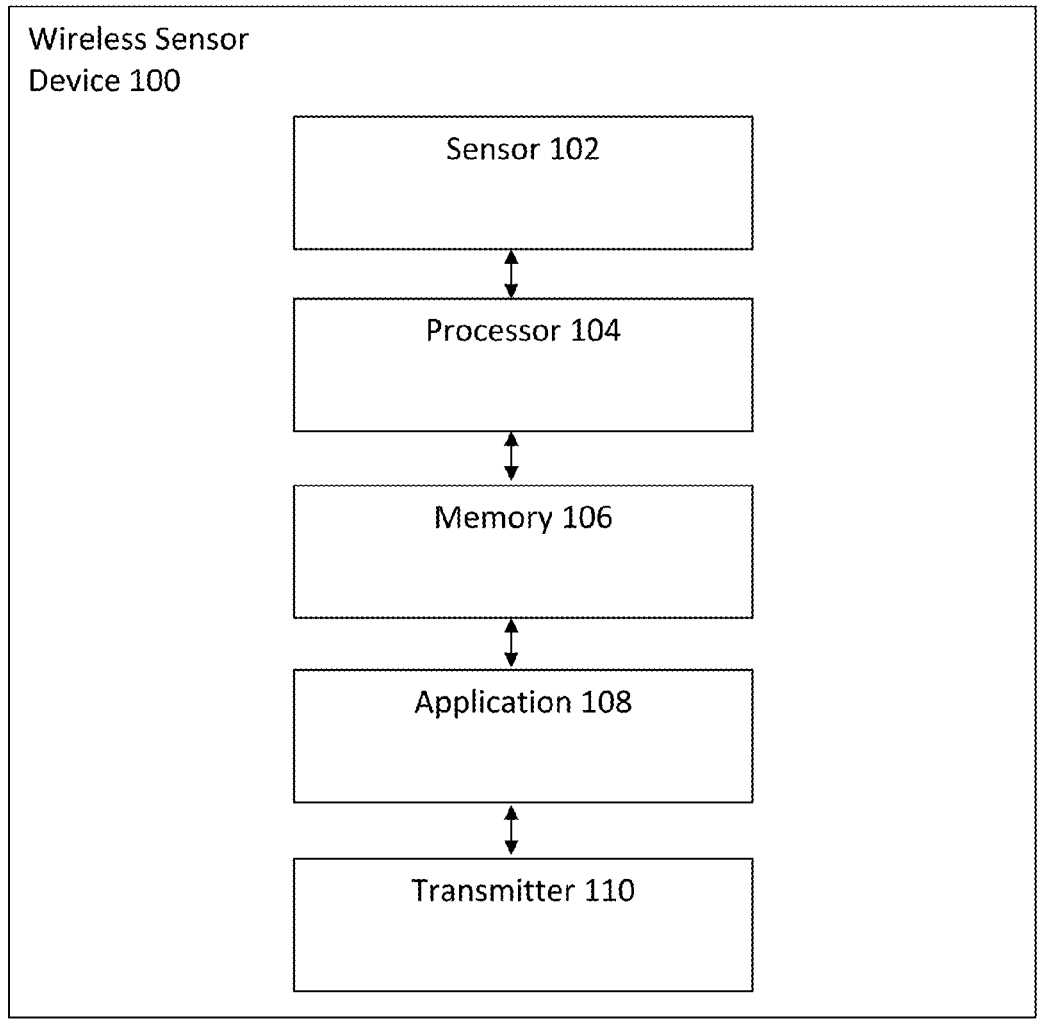
FIG. 1 illustrates a wireless sensor device in accordance with an embodiment.

The present invention relates to sensors, and more particularly, to a sensor device utilized to measure respiratory rate using a combination of respiration signals. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

Utilizing a combination of sensors and signals to estimate respiratory rate (RR) provides increased accuracy over the conventional utilization of any single sensor/signal. A method and system in accordance with the present invention's combination requires knowledge of the quality of the respiratory signal obtained from each individual sensor. The respiratory signals from a variety of sources can be utilized as inputs to the method and system in accordance with the present invention. These sources include but are not limited to mechanical signals from a chest-mounted accelerometer, EKG-derived respiration signals, bend sensors, stretch sensors (respiratory inductance plethysomography), impedance pneumography, flow sensors, and $CO_2$ sensors.

A method and system in accordance with the present invention determines a person's respiratory rate using respiration signals derived from a plurality of sources. In one embodiment, the plurality of sources include a chest-mounted accelerometer where the correct axis is perpendicular to gravity, a QRS area/amplitude where the area/amplitude of the QRS complex of an EKG signal is computed, a respiratory sinus arrhythmia (RSA) where times between subsequent R peaks of the EKG signal (R-R intervals) are computed, and any other respiration signals of interest.

After a wireless sensor device attached to a person and the wireless sensor device detects a plurality of respiration signals, each signal is filtered by the wireless sensor device to get activity in a respiratory frequency range. In one embodiment, the filtering is done by a lowpass filter at 0.7 Hertz (Hz). An application stored on the wireless sensor device conducts peak-picking of each respiration signal to detect a number of breaths that the person takes and computes the respiratory rate by using a changing threshold based on a standard deviation of the signal at that time point.

The wireless sensor device analyzes the respiratory rate and determines a quality metric between 0 and 1 based on regularity of minima times and amplitudes and a noisiness of the respiration signal. The quality metric enables the wireless sensor device to determine whether each derived respiratory rate can be trusted. The quality metric is inversely correlated to expected error with 0 denoting high error and 1 denoting low error. Additionally, smoothing is performed on the respiratory rate to reduce effects of missed/extraneous peaks using a trimmed mean.

One of ordinary skill in the art readily recognizes that a variety of wireless sensor devices can be utilized to measure the person's respiratory rate including portable wireless sensor devices with embedded circuitry in a patch form factor and that would be within the spirit and scope of the present invention.

To describe the features of the present invention in more detail, refer now to the following description in conjunction with the accompanying Figures.

FIG. 1 illustrates a wireless sensor device 100 in accordance with an embodiment. The wireless sensor device 100 includes a sensor 102, a processor 104 coupled to the sensor 102, a memory 106 coupled to the processor 104, an application 108 coupled to the memory 106, and a transmitter 110 coupled to the application 108. The sensor 102 obtains data from the user and transmits the data to the memory 106 and in turn to the application 108. The processor 104 executes the application 108 to process ECG signal information of the user. The information is transmitted to the transmitter 110 and in turn relayed to another user or device.

In one embodiment, the sensor 102 comprises two electrodes to measure cardiac activity and an accelerometer to record physical activity and posture and the processor 104 comprises a microprocessor. One of ordinary skill in the art readily recognizes that a variety of devices can be utilized for the processor 104, the memory 106, the application 108, and the transmitter 110 and that would be within the spirit and scope of the present invention.

Figure 2:
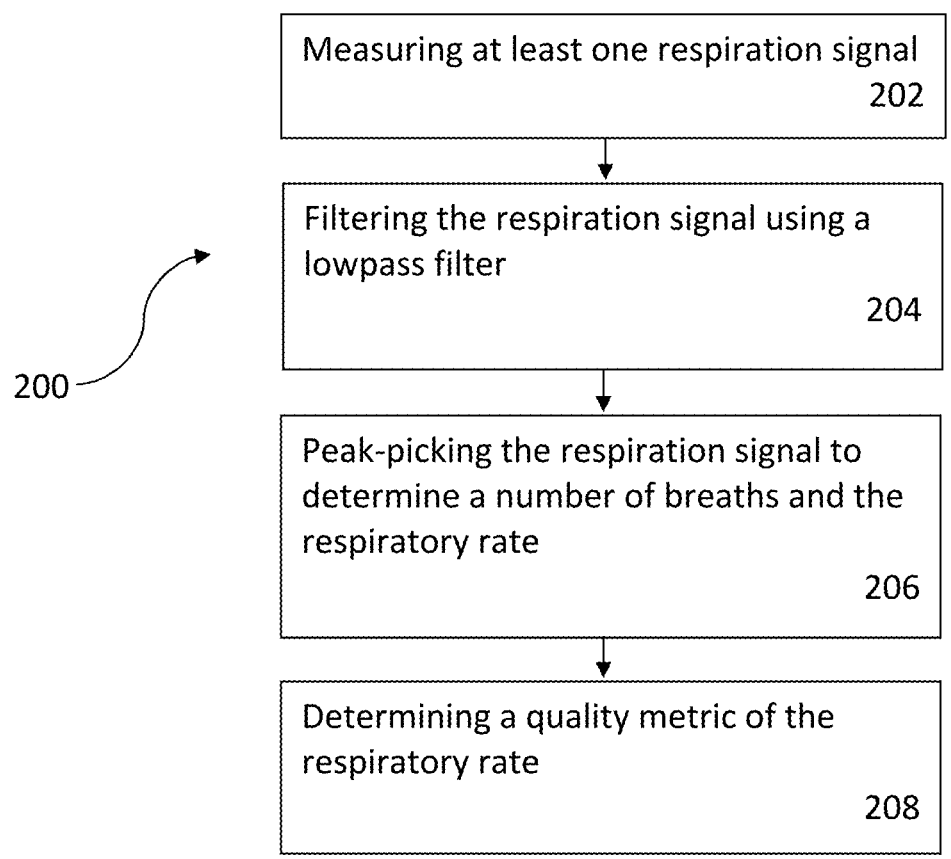
FIG. 2 illustrates a flow chart of a method for measuring respiratory rate in accordance with an embodiment.

FIG. 2 illustrates a flow chart of a method 200 for measuring respiratory rate in accordance with an embodiment. Referring to FIGS. 1 and 2 together, the method 200 comprises the wireless sensor device 100 measuring at least one respiration signal, via 202, and filtering the respiration signal using a lowpass filter, via 204. The method 200 includes peak-picking the respiration signal to determine a number of breaths and the respiratory rate, via 206, and determining a quality metric of the respiratory rate, via 208. In one embodiment, at least one respiration signal is derived from a variety of sources including but not limited to a chest-mounted accelerometer, a QRS-area and a QRS-amplitude of an EKG signal, and a respiratory sinus arrhythmia (RSA).

With a chest-mounted accelerometer embedded within a wireless sensor device that has been attached to a person, breathing can be detected during periods of low activity. During inspiration, the chest expands and the angle of the accelerometer to gravity changes slightly. An angle change of θ yields a magnitude change of sine approximately equal to θ when θ is close to 0. When the person is upright or lateral, the best axis to examine is the anterior-posterior axis and when the person is supine, the best axis to examiner is the inferior-superior axis (head to toe).

The respiration signal derived from a chest-mounted accelerometer has minima and maxima that correspond to inspiration and expiration. The minima and maxima can correspond to either the inspiration or the expiration. The magnitudes of the respiration signal's peaks are not uniform so a method and system in accordance with the present invention utilizes an accelerometer respiration process with a time-varying threshold based on a standard deviation of the respiration signal in a small predetermined time period window. By determining differences between the peak times of the respiration signal, an instantaneous respiratory rate is computed.

Figure 3:
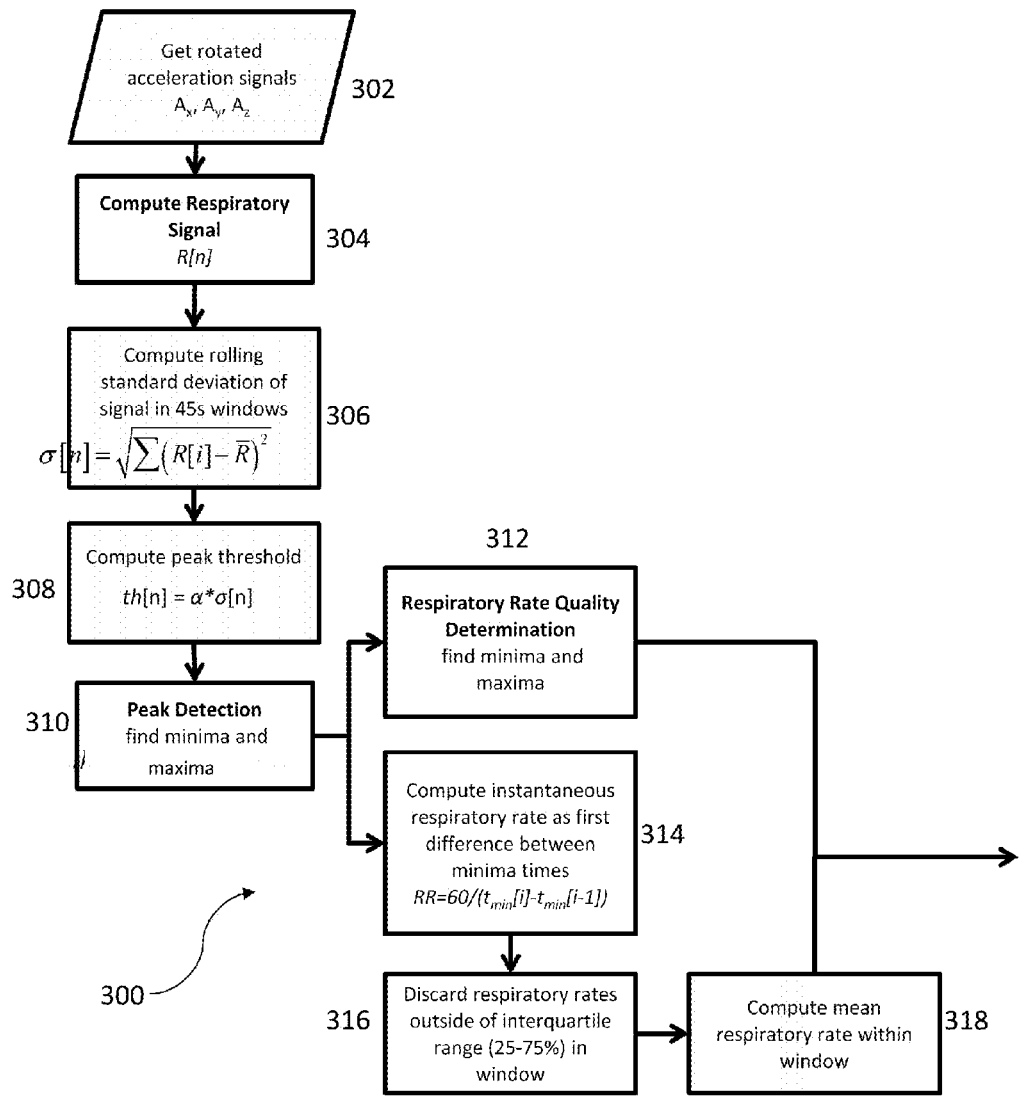
FIG. 3 illustrates a flow chart of an accelerometer respiration process in accordance with an embodiment.

FIG. 3 illustrates a flow chart of an accelerometer respiration process 300 in accordance with an embodiment. The accelerometer respiration process 300 obtains rotated acceleration signals $A_x$, $A_y$, $A_z$, via 302, and computes respiratory signal (R[n]) based upon the correct axis that is perpendicular to gravity, via 304. A rolling standard deviation ($\sigma[n]$) of the respiratory signal R[n] is computed within a predetermined 45 second window (n) per the equation: $\sigma[n]=\sqrt{\Sigma(R[i]-\overline{R})^2}$, via 306. Using the rolling standard deviation, a peak threshold is computed per the equation: $th[n]=\alpha * \sigma[n]$, via 308, where $\alpha$ is the number of standard deviations (e.g. 1.3) for the peak threshold $th[n]$.

After computing the peak threshold, a peak detection process is utilized to determine the minima and maxima of the respiratory signal R[n], via 310. A respiratory rate quality metric is determined using a number of features that judge the regularity of the respiration peaks, via 312, and an instantaneous respiratory rate (RR) is computed as the first difference between minima times per the equation: $RR=60/(t_{min}[i]-t_{min}[i-1])$, via 314. Respiratory rates outside of an interquartile range (25-75%) within the predetermined 45 second window are discarded, via 316, and a trimmed mean respiratory rate is computed, via 318, to smooth the computed instantaneous RR.

In one embodiment, the respiratory signal (R[n]) computation via 304 determines an axis that is perpendicular to a gravity vector ($G=[g_x, g_y, g_z]$). When a person is upright, the axis that is perpendicular to gravity is the Z axis (anterior-posterior axis) where $G\times[1;0;0]=[0;0;1]$. When a person is supine, the axis that is perpendicular to gravity is the Y axis (inferior-superior axis) where $G \times [1;0;0]=[0;1;0]$. When a person is lateral decubitus, the axis that is perpendicular to gravity is empirically found as the Z axis where $G \times [0;1;0]=[0;0;1]$. Thus, the more that gravity is pointing in the X direction, the greater the contribution of the Y axis to the cross product.

In this embodiment, low-pass filter accelerations below 0.02 Hz for gravity G and low-pass filter accelerations below 0.7 Hz for respiration $A_{LP}$ are determined. The angle $\theta$ between the gravity and the X axis is computed per the equation: $\theta=\cos^{-1}(\vec{G}\cdot\vec{i})=\cos^{-1}g_x$. Using $\theta$, the perpendicular-to-gravity direction for the respiration signal is computed per the following set of equations, where P is the direction for computing the respiration signal, and $C=\|\vec{g}\times[\sin\theta\cos\theta\ 0]^T\|$:

$$P = \vec{G} \times \begin{bmatrix} \sin\theta \\ \cos\theta \\ 0 \end{bmatrix} \Big/ C \qquad (1)$$

$$P = \vec{G} \times \begin{bmatrix} \sqrt{1-g_x^2} \\ g_x \\ 0 \end{bmatrix} \Big/ C$$

$$P = \begin{bmatrix} -g_x g_z \\ g_z\sqrt{1-g_x^2} \\ g_x^2 - g_y\sqrt{1-g_x^2} \end{bmatrix} \Big/ C.$$

Using P, an accelerometer-based respiratory signal is computed per the following set of equations, where R is the respiratory signal:

$$R = P \cdot A_{LP} \quad (2)$$

$$R = \begin{bmatrix} -g_x g_z \\ g_z\sqrt{1-g_x^2} \\ g_x^2 - g_y\sqrt{1-g_x^2} \end{bmatrix} \cdot A_{LP}/C.$$

In one embodiment, the peak detection/peak-picking process that is utilized to determine the minima and maxima of the respiratory signal via 310 utilizes a changing threshold based on a standard deviation of the respiration signal at a certain time point. The peak detection process ensures that a peak-to-peak amplitude of the respiration signal is greater than a certain threshold (th[n]) that depends on the variability of the respiration signal.

Figure 4:
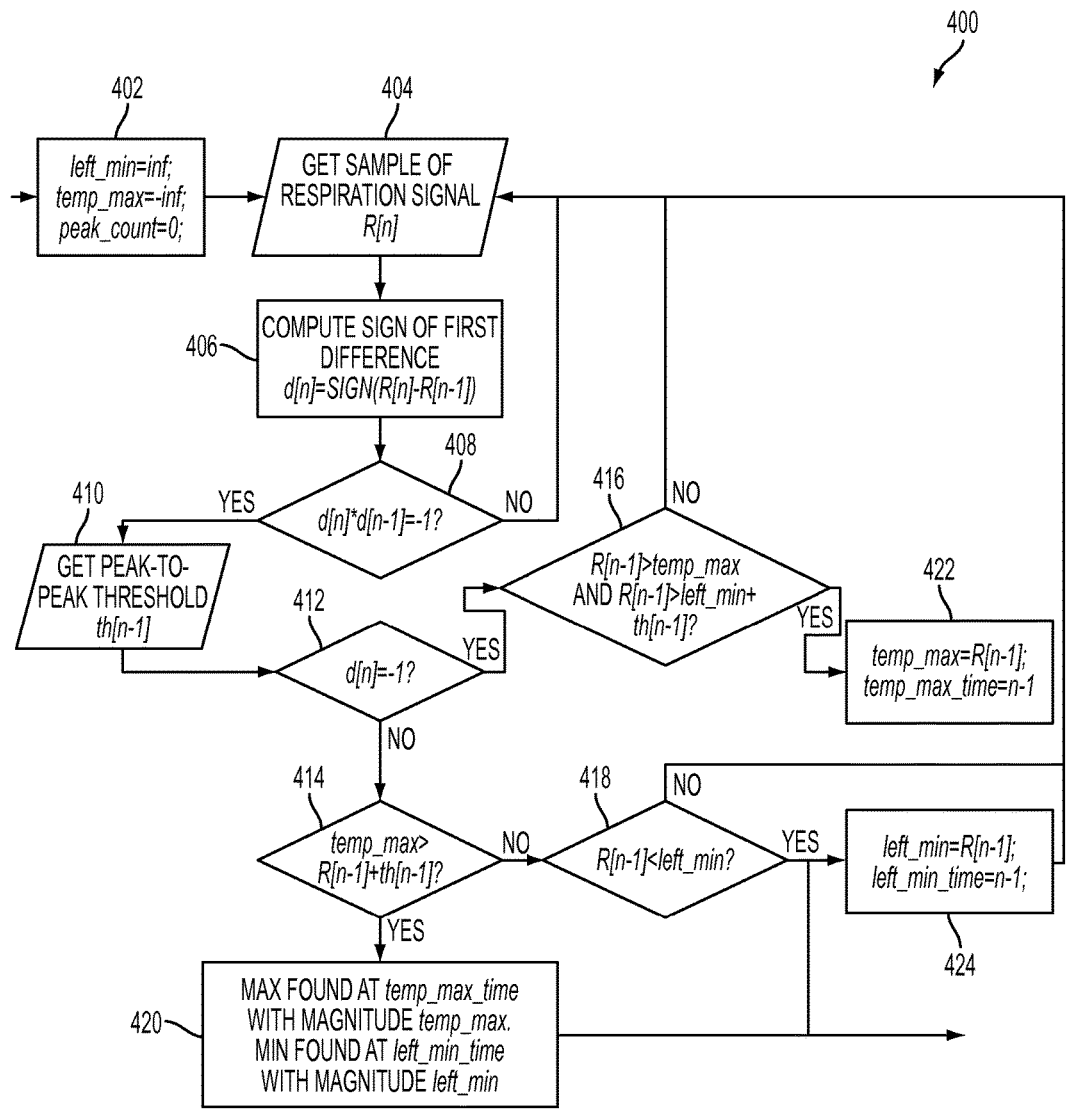
FIG. 4 illustrates a flow chart of a peak detection process in accordance with an embodiment.

FIG. 4 illustrates a flow chart of a peak detection process 400 in accordance with an embodiment. The peak detection process 400 can be utilized for respiration signals from a variety of sources including but not limited to the chest-mounted accelerometer, QRS-area, and RSA. The peak detection process 400 sets left_min=inf, temp_max=inf, and peak_count=0 via 402 and obtains a sample of a respiration signal R[n] via 404. A sign of the first difference of the respiration signal is computed per the equation: d[n]=sign (R[n]−R[n−1]), via 406.

The peak detection process 400 analyzes whether d[n]*d[n−1]=−1 via 408. If no (d[n]*d[n−1] does not equal −1), the process 400 returns back to 404 to get another sample of the respiration signal R[n]. If yes (d[n]*d[n−1]=−1), the process 400 determines a peak-to-peak threshold th[n−1] via 410 and analyzes whether d[n]=−1 via 412. If no (d[n] does not equal −1), the process 400 analyzes whether temp_max>R[n−1]+th[n−1] via 414 and if yes (d[n]=−1), the process 400 analyzes whether R[n−1]>temp_max and R[n−1]>left_min +th[n] via 416. If no (R[n−1] is not greater than temp_max or R[n−1] is not greater than left_min +th[n]), then the process 400 returns back to 404 to get another sample of the respiration signal R[n]. If yes (R[n−1]>temp_max and R[n−1]>left_min+th[n]), then the process 400 sets temp_max=R[n−1] and temp_max_time=n−1 and returns back to 404 to get another sample of the respiration signal R[n].

If temp_max>R[n−1]+th[n−1], then the process 400 determines that a maxima is found at temp_max_time with a magnitude of temp_max and also determines that a minima is found at left_min_time with a magnitude of left_min via 420. If temp_max is not greater than R[n−1]+th[n−1], then the process 400 analyzes whether R[n−1]<left_min via 418. If no (R[n−1] is not less than left_min), then the process 400 returns back to 404 to get another sample of the respiration signal R[n]. If yes (R[n−1]<left_min), then the process sets left_min=R[n−1] and left_min_time=n−1 and then returns back to 404 to get another sample of the respiration signal R[n].

Therefore, if the peak detection process 400 determines that the first difference of the respiration signal (R[n]−R[n−1]) moves from positive to negative, the process 400 analyzes whether a peak of the respiration signal is greater than left_min+th[n] and whether the peak is greater than the last temp_max. If both of these conditions are met, the peak is set as the new temp_max. If the peak detection process 400 determines a derivative of the respiration signal moves from negative to positive, the process 400 analyzes whether the valley is less than th[n] of the temp_max and if so, the process 400 sets the temp_max as an actual maxima and the left_min as an actual minima. Otherwise, if the valley is less than the previous left_min, then the process 400 sets the valley as the new left_min. Every time a minima/maxima pair is found, the process 400 sets the current temp_max to −∞ and sets the current left_min to ∞.

In one embodiment, the respiratory rate quality metric determination via 312 is derived within a predetermined time period (e.g. 45 seconds) and is derived based on features including but not limited to a coefficient of variation (standard deviation over the mean) of a difference in minima times ($c_t$), a coefficient of variation (standard deviation over the mean) of peak-to-peak values ($c_p$), a mean peak-to-peak value ($m_p$), and a ratio of a number of picked extrema to a total number of all local extrema ($r_{ext}$). In this embodiment, the quality metric is weighted using previously learned weights and transformed using an exponential to get the quality metric to a value between 0 and 1.

The quality metric for each input signal is estimated in 45 second windows using the aforementioned features that judge the regularity of the respiration peaks. A smaller $c_t$ equates to more regular peak times and thus a higher respiration signal quality. A smaller $c_p$ equates to more regular peak heights and thus a higher respiration signal quality. A larger $m_p$ indicates motion artifacts/noise and thus a lower respiration signal quality. A $r_{ext}$ closer to 1 indicates the respiration signal has a minimal spurious peaks and thus a higher respiration signal quality.

The features are weighted using previously learned weights to get an estimation of the error (E) in the respiration signal. Weights are learned by least-squares regression on a collected dataset so that the learned weights allow for the best prediction of the error. In one embodiment, E is computed as $E=w_1*c_t+w_2*c_p+w_3*m_p+w_4*r_{ext}+w_5$ where typical weights include but are not limited to $w_1=3.8$, $w_2=7.9$, $w_3=9.8$, $w_4=8.4$, and $w_5=8.3$. The error (E) is transformed using an exponential to get a quality metric (Q) between 0 and 1 per the equation $Q=e^{-E/\gamma}$, where $\gamma=5$. The γ parameter is variable depending on the desired correspondence between estimated error and quality. The smaller the value of γ, the more the quality is reduced for a given error. When the estimated error (E) is high, Q gets closer to 0 which indicates a lower respiration signal quality. When the estimated error (E) is low and closer to 0, then Q gets closer to 1 which indicates a higher respiration signal quality.

If the mean peak-to-peak value $m_p$ is below a threshold min_p2p, the quality of the respiration signal (Q) is reduced by multiplying it by $m_p$/min_p2p. Because $m_p$/min_p2p is less than 1, the quality will become smaller. The small peak-to-peak values occur when the respiration signal is too small, and near noise, thereby making it more difficult to accurately estimate a respiratory rate from this respiration signal. Therefore, by reducing the quality metric in these situations, the algorithm is prevented from relying upon these signals.

Figure 5:
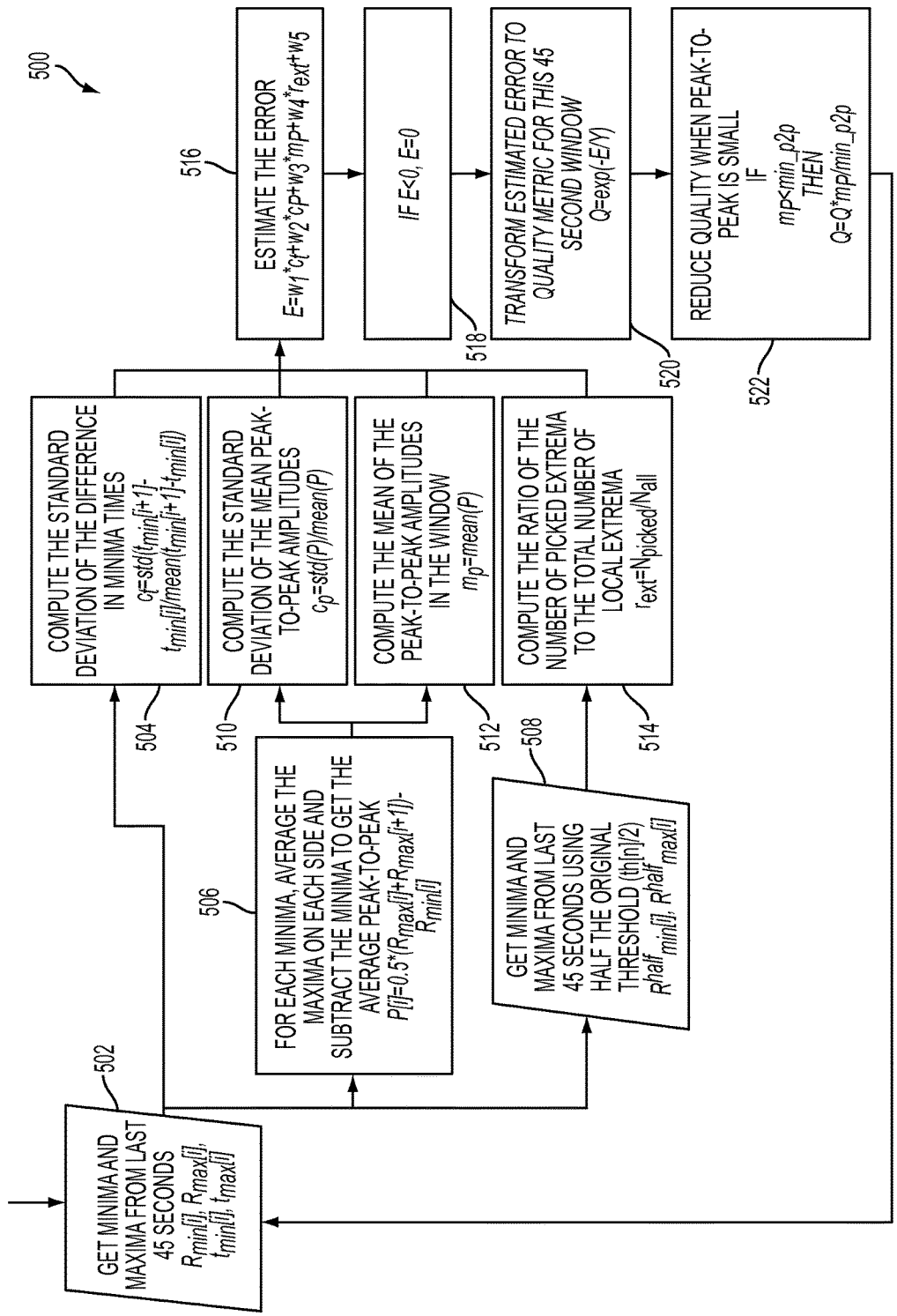
FIG. 5 illustrates a flow chart of a quality metric process in accordance with an embodiment.

FIG. 5 illustrates a flow chart of a quality metric process 500 in accordance with an embodiment. The quality metric process 500 obtains minima and maxima within a 45 second time window of the respiration signal as $R_{min}[i]$, $R_{max}[i]$, $t_{min}[i]$, and $t_{max}[i]$ via 502. A coefficient of variation of the difference in minima times ($c_t$) is computed by the quality metric process 500 per the equation: $c_t=\text{std}(t_{min}[i+1]-t_{min}[i])/\text{mean}(t_{min}[i+1]-t_{min}[i])$, via 504. For each minima, the process 500 averages the maxima on each side and subtracts the minima to get an average peak-to-peak (P[i]) per the equation: $P[i]=0.5*(R_{max}[i]+R_{max}[i+1])-R_{min}[i]$, via 506. The process 500 also obtains the minima and maxima from the last 45 second time window ($R^{half}_{min}[i]$ and $R^{half}_{max}[i]$) using half the original threshold (th[n]/2) via 508.

Once the average peak-to-peak P[i] is computed, the process 500 computes a coefficient of variation of the mean peak-to-peak amplitudes ($c_p$) per the equation: $c_p=std(P)/mean(P)$, via 510, and computes a mean of the peak-to-peak amplitudes in the 45 second time window per the equation: $m_p=mean(P)$, via 512. Once the minima and maxima from the last 45 second time window are obtained, the process 500 computes a ratio of the number of picked extrema to the total number of local extrema per the equation: $r_{ext}=N_{picked}/N_{all}$, via 514.

Following the computation of $c_t$, $c_p$, $m_p$, and $r_{ext}$, the process 500 estimates an error (E) per the equation: $E=w_1*c_t+w_2*c_p+w_3*m_p+w_4*r_{ext}+w_5$, via 516, and sets E=0 if E is less than 0 via 518. The process 500 transforms the estimated error (E) to a quality metric (Q) for the current 45 second time window per the equation: $Q=e^{-E/\gamma}$, via 520. The process 500 reduces the quality of the respiration signal when peak-to-peak is small if $m_p$<min_p2p to result in the equation $Q=Q*m_p$/min_p2p via 522.

Figure 6:
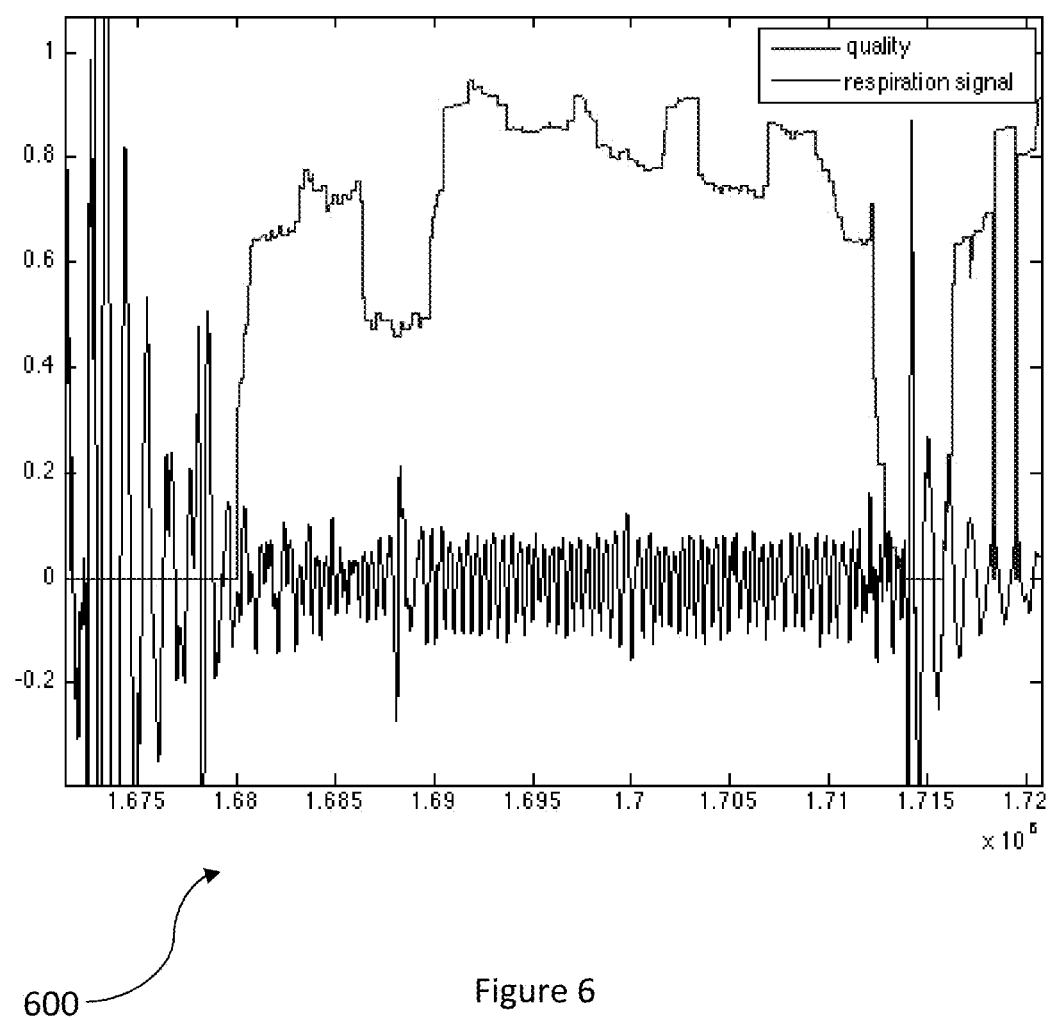
FIG. 6 illustrates a diagram that compares the quality metric to the respiration signal in accordance with an embodiment.

The quality metric process 500 can be utilized for respiration signals from a variety of sources including but not limited to the chest-mounted accelerometer, a QRS-area, a QRS-amplitude, and an RSA. For the varying respiration signals, the weights for estimating the error (E) are calibrated for the particular respiration signal that is utilized. One of ordinary skill in the art readily recognizes that large motion artifacts in the accelerometer (or other respiration signal sourcing mechanism) data reduces the quality. FIG. 6 illustrates a diagram 600 that compares the quality metric to the respiration signal in accordance with an embodiment. As the respiration signal experiences noise during the start and end of the time window, the quality metric is closer to 0 but as the respiration signal experiences minimal noise during the middle of the time window, the quality metric is closer to 1.

In addition to deriving a respiration signal from a chest-mounted accelerometer, the respiration signal can also be derived via a QRS wave of an EKG signal. In one embodiment, the sensor 102 comprises electrodes that enable the wireless sensor device 100 to measure an EKG signal of a person when attached. The QRS wave of the EKG is modulated with respiration due to the mechanical effect of breathing on the heart. Breathing shifts the heart within the thorax and changes the cardiac axis which results in a change in QRS-amplitude during inspiration/expiration.

In one embodiment, the QRS-area or QRS-amplitude is computed as a measure of modulation of the QRS wave due to respiration using a QRS respiration process. In this embodiment, an EKG signal is detected by the wireless sensor device 100 and the EKG signal is filtered using 20 Hz of high-pass filtering. After the filtering, R-wave peaks are detected and an R-wave peak is analyzed utilizing a predetermined time window (e.g. 100 milliseconds) that is centered around the R-wave peak.

The absolute value of the respiration signal in the predetermined time window is summed which results in a single QRS-area number for each QRS complex. These numbers are resampled at 4 Hz to result in a smoother and more accurate respiratory rate. For the QRS-amplitude, the minimum value within the 100 millisecond (ms) predetermined time window is subtracted from the maximum value and the resulting output is resampled at 4 Hz to result in a smoother and more accurate respiratory rate.

Figure 7:
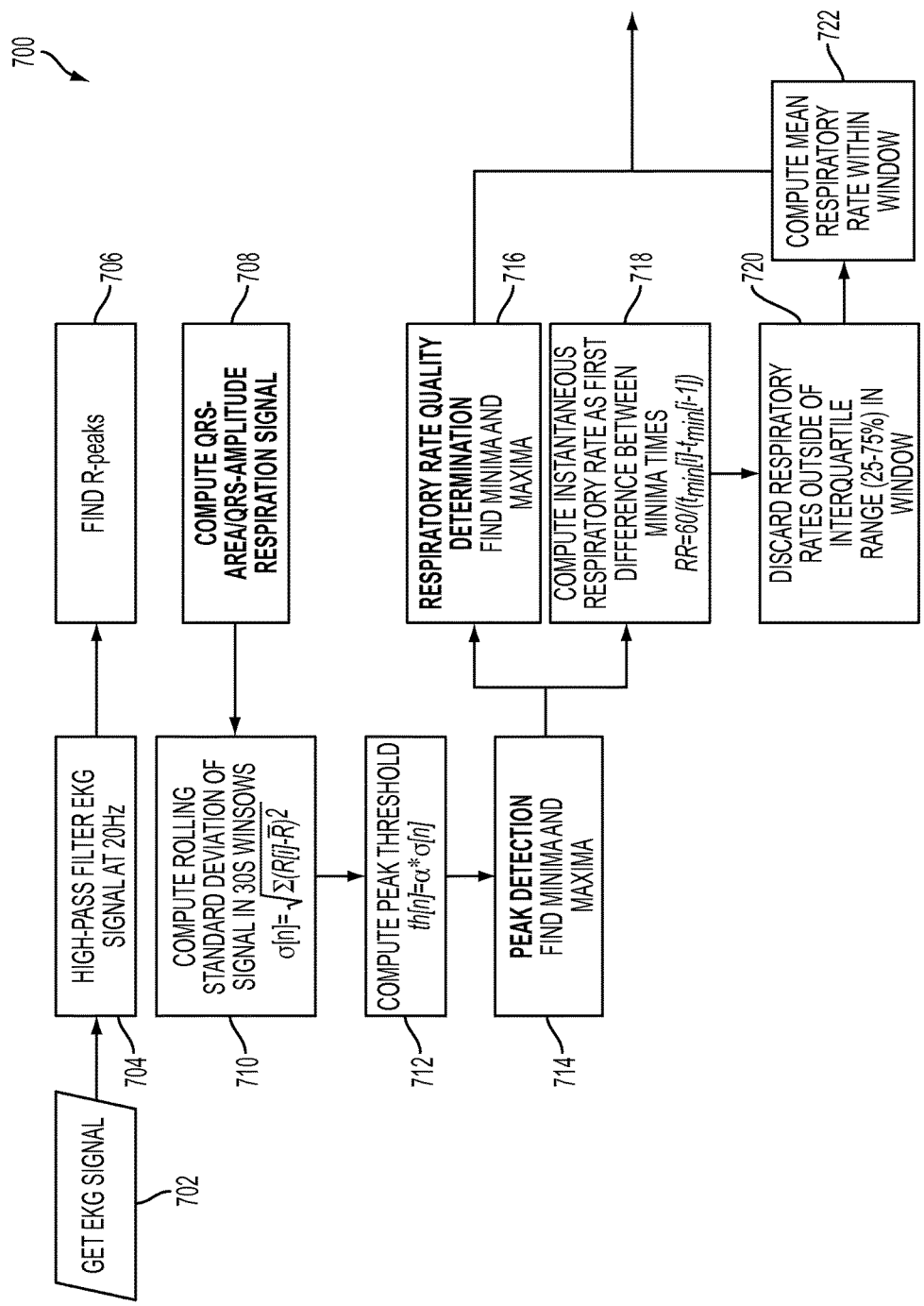
FIG. 7 illustrates a flow chart of a QRS respiration process 700 in accordance with an embodiment.

The QRS respiration process is similar to the accelerometer respiration process 300 except for the computation of the respiration signal. A quality metric process of the QRS based respiration signal is generated using the same computations as the quality metric process 500. FIG. 7 illustrates a flow chart of a QRS respiration process 700 in accordance with an embodiment. The QRS respiration process 700 obtains an EKG signal via 702 and high-pass filters the EKG signal at 20 Hz via 704. The QRS respiration process 700 determines R-peaks via 706 and computes a QRS-area/QRS-amplitude respiration signal via 708. The steps 710-722 of the QRS respiration process 700 resemble steps 306-318 of the accelerometer respiration process 300.

In one embodiment, the QRS-area computation via 708 comprises obtaining the latest R-peak time $t_R$ and extracting a 100 ms time period window around the current R-peak to determine a current QRS wave. An absolute value of the QRS wave is determined per the equation and an area of the QRS wave is computed by summing the absolute values of the EKG signal within the 100 ms time period window per the equation $$\sum_{i=t_R-50ms}^{t_R+50ms}|EKG[i]|.$$

The QRS-area derived respiration signal is resampled at 4 Hz to determine the QRS-area derived respiratory rate.

In one embodiment, the QRS-amplitude computation via 708 comprises the same process except that the amplitude is computed as a maximum/minimum instead of summing the values in the 100 ms time period window. Therefore, after obtaining the latest R-peak time and extracting a 100 ms time period window around the current R-peak, the maximum and minimum values in the 100 ms time period window are determined as $QRS_{MAX}$ and $QRS_{MIN}$. The QRS-amplitude is computed as the maximum minus the minimum or $QRS_{MAX}-QRS_{MIN}$ and the QRS-amplitude derived respiration signal is resample at 4 Hz to determine the QRS-amplitude derived respiratory rate.

In addition to deriving a respiration signal from a chest-mounted accelerometer and the QRS wave of an EKG signal, the respiration signal can also be derived from heart rates computed via an EKG signal. Besides changing the QRS-area/QRS-amplitude, breathing also changes the heart rate such that the heart rate increases during inspiration and decreases during expiration. This is known as the respiratory sinus arrhythmia (RSA). The R-R intervals of the EKG signal are calculated to determine another signal that is correlated to breathing as R-R intervals decrease with inspiration and increase with expiration.

In one embodiment, an RSA respiration process is utilized to determine a respiration signal from heart rates computed from an EKG signal. The RSA respiration process is similar to the QRS-area computation via 708 except that instead of computing the area of each QRS complex, the time between the current and last QRS complex is computed and then resampled at 4 Hz to determine the RSA derived respiratory rate. RSA decreases with age thereby making the RSA respiration process derived respiration signal less reliable and increasing the importance of the quality metric determination.

Respiration signals can be determined via the aforementioned accelerometer respiration process 300 (resulting in $RR_{ACCEL}$), the QRS respiration process 700 (resulting in $RR_{QRS}$), and the RSA respiration process (resulting in $RR_{RSA}$). Using the outputted quality metric for each of these respiration signals, a combined and weighted respiratory rate ($RR_{weighted}$) is computed per the equation:

$$RR_{weighted} = RR_{ACCEL}\frac{Q_{ACCEL}}{Q_{ACCEL} + Q_{QRS} + Q_{RSA}} +$$

$$RR_{QRS}\frac{Q_{QRS}}{Q_{ACCEL} + Q_{QRS} + Q_{RSA}} + RR_{RSA}\frac{Q_{RSA}}{Q_{ACCEL} + Q_{QRS} + Q_{RSA}}.$$

Figure 8:
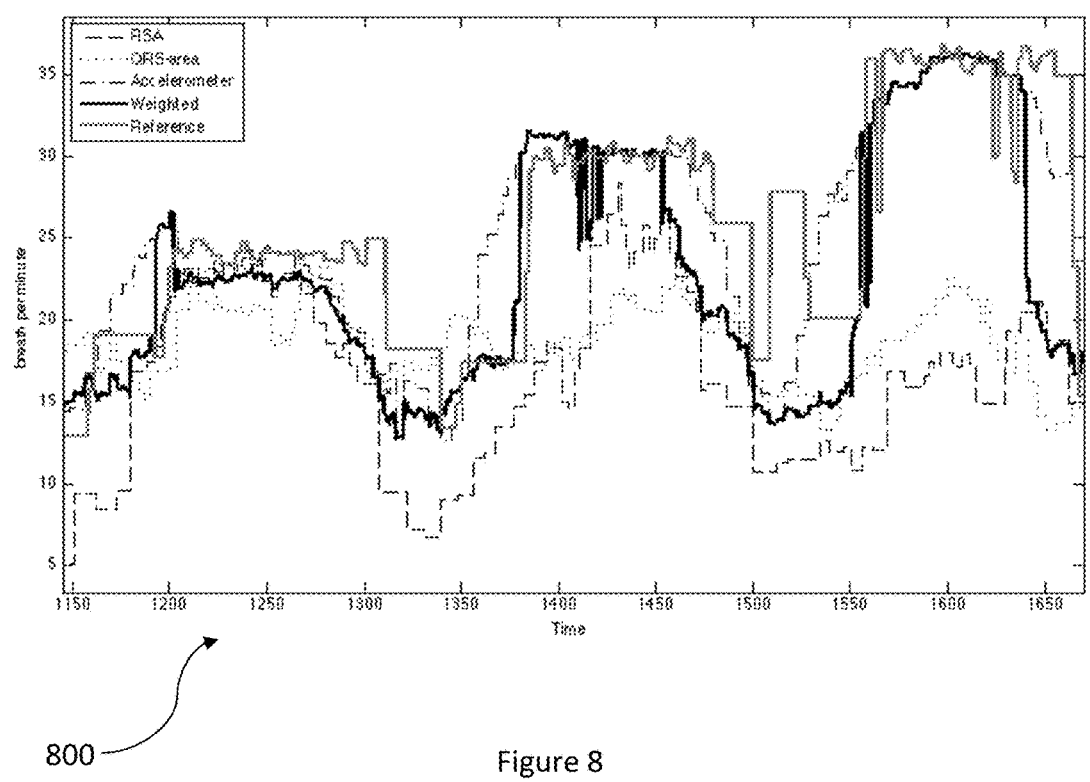
FIG. 8 illustrates a diagram of respiration signal computations in accordance with an embodiment.

Each respiration rate is weighted by a value defined as each associated quality metric divided by the sum of all of the quality metrics. For example, if $RR_{ACCEL}$ is unreliable due to heavy motion artifacts and noise, $Q_{ACCEL}$ will be close to 0 and that component of the $RR_{weighted}$ equation will not contribute much to the final respiratory rate. FIG. 8 illustrates a diagram 800 of respiration rate computations in accordance with an embodiment. In addition to the combined and weighted respiratory rate ($RR_{weighted}$), the diagram 800 includes respiratory rates derived from an accelerometer, QRS-area, RSA, and a NOX RIP-band reference.

Weighting the respiration rates that are derived by the accelerometer ($RR_{ACCEL}$) and the EKG signals ($RR_{QRS}$ and $RR_{RSA}$) by their respective quality metrics overcomes issues such as motion artifacts, increased respiration rates, and patient ages that can diminish respiration signal quality. For example, utilizing the $RR_{weighted}$ combination results in an output that weighs the $RR_{ACCEL}$ less during the presence of motion artifacts, weighs $RR_{QRS}$ less during high respiration rates, and weighs $RR_{RSA}$ less if the patient is elderly.

QRS-area and RSA derived respiration signals cannot detect breathing rates of higher than half the heart rate (HR) because they are EKG-based. This is known as cardiac aliasing. A fundamental property of all sampled signals is that it is not possible to distinguish any frequency content that is larger than ½ the sampling rate ($F_s$) which is the Nyquist Frequency (NS). Any frequency content above NS cannot be reliably distinguished, and this is called aliasing. The heart rate serves as the sampling rate of the EKG-derived respiration signal and respiration rates above ½HR cannot be detected. As a result, if the respiration rate is above ½HR, then only the respiratory rate derived from the accelerometer ($RR_{ACCEL}$) is utilized per the equation:

IF ($RR_{ACCEL}$>HR/2) and $Q_{ACCEL} \geq \tau_{ACCEL}$, then
$RR_{weighted} = RR_{ACCEL}$.

As above described, the method and system allow for measuring a respiratory rate using a combination of respiration signals. A wireless sensor device determines a plurality of respiration signals from a variety of sources including but not limited to a chest-mounted accelerometer, a QRS-area of an EKG signal, a QRS-amplitude of an EKG signal, and an RSA. The wireless sensor device then computes a quality metric for each of the plurality of respiration signals, and combines the plurality of quality metrics to compute a weighted respiratory rate. The weighted respiratory rate is an accurate measurement of a person's respiratory rate that reduces the effects of quality issues including but not limited to motion artifacts and the person's age.

A method and system for measuring respiratory rate has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to cause the receiver to perform the functions described herein.

Furthermore, embodiments may take the form of a computer program product accessible from a computer-usable or computer-readable storage medium providing program code or program instructions for use by or in connection with a computer or any instruction execution system. For the purposes of this description, a computer-usable or computer-readable storage medium can be any apparatus that can contain, store, communicate, propagate, or transport the program for use by or in connection with the instruction execution system, apparatus, or device.

The computer-readable storage medium may be an electronic, magnetic, optical, electromagnetic, infrared, semiconductor system (or apparatus or device), or a propagation medium. Examples of a computer-readable storage medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk-read/write (CD-RAN).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A system for determining respiratory rates of a user, the system comprising:
    at least one electrode adapted to be coupled to the user, wherein the at least one electrode measures at least one respiration signal,
        wherein to measure at least one respiration signal is to measure a plurality of respiration signals to determine a plurality of respiration rates ($RR_{1 \ldots N}$), wherein the application further causes the processor to:
            determine a quality metric ($Q_{1 \ldots N}$) for each of the plurality of respiration rates; and
            combine the plurality of respiration rates by weighting the quality metric for each of the plurality of respiration rates based on a quality process to calculate a weighted respiration rate ($RR_{weighted}$);
    a processor coupled to the at least one electrode; and
    a memory device coupled to the processor, wherein the memory device stores an application which, when executed by the processor, causes the processor to:
    filter the at least one respiration signal measured by the at least one electrode using a lowpass filter;
    peak-pick the filtered respiration signal to determine a respiratory rate by using a standard deviation of the filtered respiration signal over a changing threshold; and
    determine a quality metric of the respiratory rate by using previously learned weights of features of the respiratory rate, wherein the features of the respiratory rate include a coefficient of variation of a difference in minima times ($c_t$), a coefficient of variation of peak-to-peak values ($c_p$), a mean peak-to-peak value ($m_p$), and a ratio of a number of picked extrema to a total number of all local extrema ($r_{ext}$).

2. The system of claim 1, wherein the at least one respiration signal is derived using any of a chest-mounted accelerometer, a QRS-area of an EKG signal, a QRS-amplitude of the EKG signal, and a respiratory sinus arrhythmia (RSA).

3. The system of claim 1, wherein the quality metric is weighted using the previously learned weights and transformed using an exponential to get the quality metric to a value between 0 and 1.

4. The system of claim 1, wherein the quality metric is derived within a predetermined time period.

5. The system of claim 4, wherein the predetermined time period is 45 seconds.

6. The system of claim 1, wherein the application further causes the processor to:
   perform a smoothing of the respiratory rate to reduce effects of missed and extraneous peaks using a trimmed mean.

7. The system of claim 1, wherein the weighted respiration rate ($RR_{weighted}$) comprises:

$$RR_{weighted} = RR_1 * (Q_1/(Q_1 + Q_2 + \ldots + Q_N)) + RR_2 * (Q_2/(Q_1 + Q_2 + \ldots + Q_N)) + RR_N * (Q_N/(Q_1 + Q_2 + \ldots Q_N)).$$

* * * * *